(12) United States Patent
Wirth et al.

(10) Patent No.: US 9,758,542 B2
(45) Date of Patent: Sep. 12, 2017

(54) PROTEIN CHROMATOGRAPHY MATRICES WITH HYDROPHILIC COPOLYMER COATINGS

(71) Applicant: PURDUE RESEARCH FOUNDATION, West Lafayette, IN (US)

(72) Inventors: Mary J. Wirth, West Lafayette, IN (US); Yimin Hua, Arlington, MA (US); Zhaorui Zhang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 12 days.

(21) Appl. No.: 14/355,595

(22) PCT Filed: Nov. 1, 2012

(86) PCT No.: PCT/US2012/063049
§ 371 (c)(1),
(2) Date: May 1, 2014

(87) PCT Pub. No.: WO2013/067171
PCT Pub. Date: May 10, 2013

(65) Prior Publication Data
US 2014/0316108 A1    Oct. 23, 2014

Related U.S. Application Data

(60) Provisional application No. 61/554,317, filed on Nov. 1, 2011.

(51) Int. Cl.
| | |
|---|---|
| *C07K 1/22* | (2006.01) |
| *B01J 20/281* | (2006.01) |
| *C07H 1/08* | (2006.01) |
| *B01D 15/38* | (2006.01) |
| *B01J 20/283* | (2006.01) |
| *B01J 20/285* | (2006.01) |
| *B01J 20/32* | (2006.01) |
| *B01J 20/10* | (2006.01) |
| *B01J 20/28* | (2006.01) |

(52) U.S. Cl.
CPC .......... *C07H 1/08* (2013.01); *B01D 15/3809* (2013.01); *B01J 20/103* (2013.01); *B01J 20/281* (2013.01); *B01J 20/283* (2013.01); *B01J 20/285* (2013.01); *B01J 20/28016* (2013.01); *B01J 20/3204* (2013.01); *B01J 20/327* (2013.01); *B01J 20/3276* (2013.01); *C07K 1/22* (2013.01); *B01D 15/3823* (2013.01); *B01D 15/3828* (2013.01)

(58) Field of Classification Search
None
See application file for complete search history.

(56) References Cited

U.S. PATENT DOCUMENTS

| | | | |
|---|---|---|---|
| 3,808,125 A | 4/1974 | Good | |
| 4,415,631 A | 11/1983 | Schutijser | |
| 5,362,859 A | 11/1994 | Zale | |
| 6,451,260 B1 | 9/2002 | Dusterhoft et al. | |
| 7,303,821 B1* | 12/2007 | Huang | 428/446 |
| 2005/0029196 A1 | 2/2005 | Rhemrev-Boom | |
| 2007/0161121 A1* | 7/2007 | Schuchard et al. | 436/514 |
| 2011/0021756 A1 | 1/2011 | Maeno | |
| 2011/0062451 A1 | 3/2011 | Ohno | |

FOREIGN PATENT DOCUMENTS

| | | |
|---|---|---|
| JP | 57171257 | 10/1982 |
| WO | WO-2010019969 A1 | 2/2010 |

OTHER PUBLICATIONS

Gong et al., Talanta (2006) 68, 666-672.*
Ranjun, Surface Modification of Silica Nanoparticles (May 2008) Dissertation, University of Akron.*
Virtanen et al., Journal of Polymer Science: Part A: Polymer Chemistry (2001) 39, 3716-3725.*
Xiao, Deqing, et al., "Kinetics of Surface-Initiated Atom Transfer Radical Polymerization of Acrylamide on Silica", Macromolecules, vol. 35, 2002, pp. 2919-2925.
Huang, Xueying, et al., "Surface-Initiated Radical Polymerization on Porous Silica", Analytical Chemistry, vol. 69, No. 22, Nov. 15, 1997, pp. 4577-4580.
International Search Report and Written Opinion dated Jan. 25, 2013 in International Application No. PCT/US2012/063049 (8 Pages).
Supplementary European Search Report dated Jun. 24, 2015, based on co-pending European Application No. 12845215 (8 Pages).

* cited by examiner

*Primary Examiner* — Marcela M Cordero Garcia
*Assistant Examiner* — Catherine Mader
(74) *Attorney, Agent, or Firm* — McCarter & English, LLP

(57) ABSTRACT

A coating of a random copolymer of acrylamide and a second monomer, e.g. glycidoxylmethacrylate, for a silica surface is described. The coating is applied to chromatographic support structures having silica based surfaces. The coating is functionalized to produce protein chromatography matrices that are particularly useful for extracting trace amounts of biomarker molecules from biological samples.

16 Claims, 3 Drawing Sheets

PROTEIN CHROMATOGRAPHY MATRICES WITH HYDROPHILIC COPOLYMER COATINGS

CROSS-REFERENCE TO RELATED APPLICATION

This patent application is a national stage application filed under 35 USC 371 of PCT/US/2012/063049, filed Nov. 1, 2012, which claims priority under 35 U.S.C. §119 to U.S. Provisional Patent Application Ser. No. 61/554,317 filed Nov. 1, 2011, all of which are incorporated herein, in entirety, by reference.

STATEMENT REGARDING FEDERALLY SPONSORED RESEARCH

This invention was made with government support under 1R21 CA139108 awarded by the National Institutes of Health. The government has certain rights in this invention.

FIELD OF THE INVENTION

The invention relates generally to the field of chromatography. In certain specific embodiments, the invention provides matrices and methods relating to protein chromatography including affinity chromatography.

BACKGROUND OF THE INVENTION

Chromatographic methods generally are used to separate and/or purify molecules of interest such as proteins, nucleic acids and polysaccharides from a mixture. For example, affinity chromatography involves passing a mixture over a matrix having bound to it a ligand specific for a target molecule in the mixture. Upon contacting the ligand, the target molecule is bound to the matrix and is retained from the mixture. Affinity chromatography provides a purification method that is highly specific, fast, economical and high yielding.

Protein chromatography methods are useful for detecting biomarkers associated with specific diseases in tissues and biological fluids. Early detection of these biomarkers is generally critical for successful treatment of disease, and the detection of these biomarkers is increasingly utilized as new biomarkers are discovered. However, biomarkers are usually present in very low concentrations in biological samples. Commercially available particles for affinity chromatography, for example, such as agarose beads and magnetic beads, are unsuitable for isolating trace amounts of these biomarkers. Accordingly, there is a need for new protein chromatography materials and methods to recover biomarkers and other target molecules present at low concentrations from solutions, in particular biological solutions such as serum or cell lysates.

SUMMARY OF THE INVENTION

The present disclosure relates to an affinity chromatography matrix having a solid support, a surface coating having a copolymer, and a binding ligand. The copolymer may include glycidoxylmethacrylate and acrylamide monomers. These monomers may be present in a defined ratio ranging from 1:5 to 1:200.

The present disclosure also relates to a method for purifying or extracting a target molecule (e.g. biomarkers, etc.) from a mixture including contacting the mixture with a matrix having a solid support, a surface coating having a copolymer, and a binding ligand, wherein the binding ligand binds to the target molecule, and recovering the target molecule by contacting the matrix with an eluent which releases the target molecule.

BRIEF DESCRIPTION OF THE DRAWINGS

FIG. 1 shows a coated silica particle that can be used as an affinity bead for affinity extraction of trace amounts of biomolecules.

DETAILED DESCRIPTION OF THE INVENTION

Figure 1:
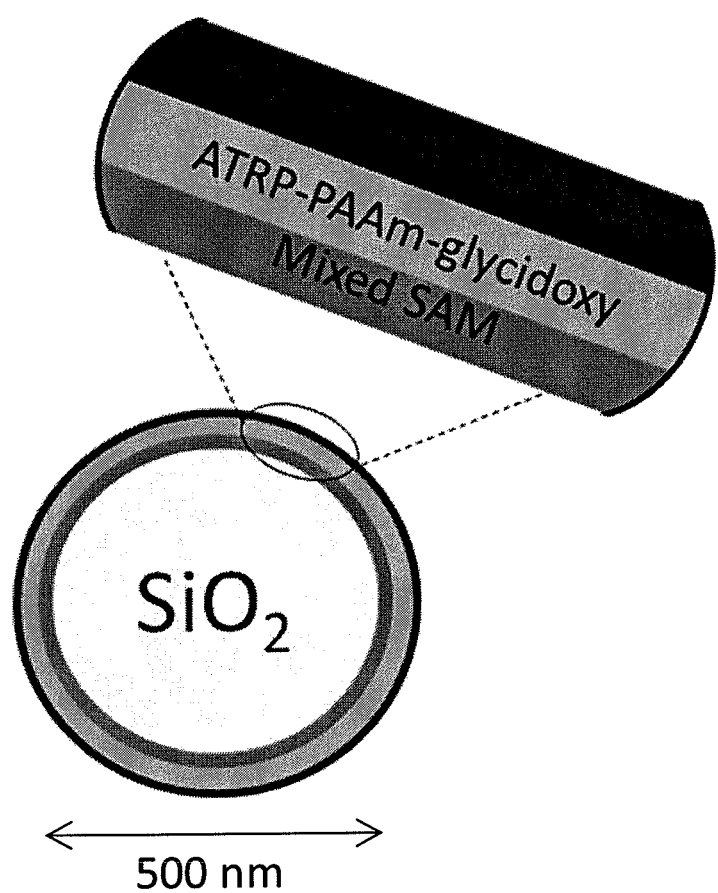
FIG. 1 shows a schematic representation of one embodiment of the present disclosure.

As used herein, the term "protein chromatography" refers to the separation of protein from a mixture using a column packed with a stationary phase through which a liquid solution flows.

As used herein, the term "affinity chromatography" refers to, in the context of protein separations and the present disclosure, chromatography which uses a ligand, e.g. an antibody, bound to the surface of a particle to selectively extract a desired molecule, e.g. protein or peptide.

As used herein, the term "copolymer" means a polymer made by using more than one monomer.

The present disclosure relates to an improved chromatography medium having the sensitivity and selectivity of an ELISA assay and methods using the same. In one embodiment, the disclosure relates to a chromatography matrix comprising a solid support, a surface coating on the solid support having a copolymer and a binding ligand.

The solid support may be a silica (silicon dioxide) based particle or monolith. For silica based particle solid support, the size of the particle(s) (or bead) may vary with the diameter of the silica particle and the thickness of the copolymer film. The diameter of the particle may range from about 50 nm to about 2 μm. Preferably, the particle has a diameter that is less than about 2 μm. In other preferred embodiments, the diameter ranges from about 200 nm to about 800 nm, and more preferably about 300 nm to about 500 nm. Spherical particles are preferred because they facilitate prediction of the surface area. A narrow particle size distribution is also preferred. For example, a particle size distribution of less than about a 10% by diameter provides that all particles centrifuge at a similar velocity. Preferably, the particles are nonporous.

The surface coating having a copolymer may be generated and attached to the surface using any method known to one skilled in the art. One method of growing the copolymer film and attaching it to the surface is by atom-transfer radical polymerization as described in Xiao and Wirth, *Macromolecules* 35: 2919-2925, 2002, which is incorporated herein by reference.

To form the surface coating having a copolymer of the present disclosure, the Xiao and Wirth method as described above may be modified by adding a second monomer to the acrylamide monomer. Polyacrylamide in the copolymer coating prevents protein and other molecules from sticking nonspecifically to the matrix itself.

Preferably, the second monomer is one that functions for use in protein chromatography by allowing attachment of one or more ligands. A variety of monomers may be included as the second monomer in the copolymer. The second monomer may contain one or more functional groups/sites that are capable of attaching the one or more ligands. In one embodiment, the second monomer is glycidoxyl methacrylate (IUPAC name: oxiran-2-ylmethyl 2-methylprop-2-enoate) or includes glycidoxyl methacrylate functional groups for binding a ligand, e.g. an antibody, which in turn may bind to the target molecule, e.g. protein of interest.

The binding sites on the second monomer may be cationic binding sites from functional groups such as carboxylic acids or sulfonic acids, or they may be anionic binding sites from amino groups. The second monomer, or the functional groups/sites on the second monomer, may include unsaturated molecules, each preferably containing at least one heteroatom. Cationic exchanges species includes, but are not limited to, methacrylic acid; acrylic acid. Diels-Alder adducts of acrylic acid; methacrylates including methyl, ethyl, butyl, isobutyl, ethylhexyl, lauryl, stearyl, hydroxyethyl, and dimethylaminoethyl; acrylates including methyl, ethyl, butyl, isobutyl, t-butyl, ethylhexyl, lauryl, stearyl, and hydroxyethyl; glycidyl methacrylate; trialkoxysilane methacrylates, such as 3-(methacryloxy)propyltrimethoxysilane and 3-(methacryloxy)propyl-triethoxysilane, methacryloxymethyltrimethoxysilane, methacryloxymethyltriethoxysilane; acrylonitrile; 2-isopropenyl-2-oxazoline; styrene; α-methylstyrene; vinyltoluene; dichlorostyrene; N-vinylpyrrolidinone, vinyl acetate, methacryloxypropyltrialkoxysilanes, methacryloxymethyltrialkoxysilanes and vinyl chloride.

Anionic exchange species include, but are not limited to, 2-(dimethylamino)ethyl methacrylate, and its many variations. The ethyl is a linker than can be as short as methyl and as long as butyl, and dimethyl groups can be hydrogens, ethyl, propyl, or butyl groups.

Other species may include, but are not limited to, maleic anhydride, dibutyl maleate, dicyclohexyl maleate, diisobutyl maleate, dioctadecyl maleate, N-phenylmaleimide, citraconic anhydride, tetrahydrophthalic anhydride, bromomaleic anhydride, chloromaleic anhydride, nadic anhydride, methylnadic anhydride, alkenylsuccinic anhydride, maleic acid, fumaric acid, diethyl fumarate, itaconic acid, citraconic acid, crotonic acid, and the respective esters, imides, salts, and Diels-Alder adducts of these compounds. These species also include silane compounds.

The relative amount of the second monomer to acrylamide in the copolymer may range from about 20:1 to about 1:200. The ratio depends on the identity of the second monomer bearing the functional group. In one embodiment, the ratio may range from about 1 to about 50, and more preferably about 1 to about 20 for moles of glycidoxylmethacrylate to moles of acrylamide. In another embodiment, the ratio may range from about 1 to about 10 to about 1 to about 1, and most preferably 1 to about 2 for moles of acrylamide to moles of methacrylate. In a further embodiment, the ratio may range from about 1 to about 10 to about 1 to about 1, and most preferably about 1 to about 2 for moles of acrylamide to moles of 2-(dimethylamino)ethyl methacrylate.

In one embodiment, the second monomer is glycidoxylmethacrylate and the preferred ratio of glycidoxylmethacrylate to acrylamide is about 1:20.

The ligand binding to the functional groups, e.g. glycidoxyl methacrylate groups, may be natural or synthetic and include, but are not limited to, antibodies and antigens, receptors and receptor binding molecules, avidin and biotin, ions and ion-binding molecules such as calcium and metal ions, nucleic acid binding moieties such as oligonucleotides, lectins and carbohydrate molecules. In one embodiment, the binding ligand is selected from the group consisting of streptavidin, protein A, protein G, and an antibody. In another embodiment, the binding ligand is selected from the group consisting of hexahistidine and a metal affinity agent, such as nickel nitriloamine.

The binding ligand may be attached to the surface coating on the solid support by any method known to one skilled in the art. Methods for functionalizing polymer coatings for the attachment of binding ligands are known in the art, for example, the coating can be reacted with ammonia, amines, amine-labeled polythymine or amine-labeled oligonucleotides. Attachment of the binding ligand produces a material useful in affinity chromatography. For example, the second monomer, e.g. glycidoxylmethacrylate, in the coating may be functionalized for use in affinity chromatography by attaching one or more types of binding ligands to the copolymer film on the outer surface of the bead.

FIG. 1 shows a schematic representation of one embodiment of the coated silica particles that can be used as affinity beads for affinity extraction of trace amounts of biomolecules. Here the mixed SAM layer is a self-assembled monolayer formed by horizontal polymerization of an initiator for polymerization and methyl groups. The chromatographic matrix does not require a mixed SAM layer. Per the Xiao and Wirth reference, the copolymer layer may be formed on the silica by standard techniques known to those skilled in the art. The term "ATRP" refers to atom transfer radical polymerization. The PAAm strongly resists protein adsorption while the glycidoxy couples the mAbs to the particles. The silica particles are highly monodisperse (+/− 3%) and spin down rapidly in a microcentrifuge.

Depending on the type(s) of binding ligands used, the resulting protein (e.g. affinity) chromatography matrix may be used to purify, extract, isolate, and/or separate specific target molecules, for example, specific proteins, peptides, nucleic acids, glycoproteins, and sugars from mixtures and solutions. For instance, the resulting affinity chromatography matrix may be particularly useful for isolating trace amounts of biomarkers from biological fluids and cell lysates.

The present disclosure also relates to a method for purifying, extracting, etc. a target molecule from a mixture comprising contacting the mixture with the protein chromatography matrix described herein, wherein the binding ligand binds to the target molecule, and recovering the target molecule by contacting the matrix with an eluent which releases the target molecule. The mixture may be blood serum, cell lysates, extracts of blood serum, extracts of cell lysates, protein pharmaceuticals not limited to but including monoclonal antibodies and insulin.

Contacting the mixture with the chromatography matrix may involve suspending the particles in a liquid sample or flowing a liquid sample through a packed column of the particles. In one embodiment, the mixture may be contacted with the matrix by pouring the mixture, or a solution containing the mixture, into a burette containing the matrix. The mixture passes through the matrix by the force of gravity, by pumping or by using a chromatograph system. In another embodiment, the mixture may be contacted with the matrix by injecting the mixture, or a solution containing the mixture, into a column containing the matrix. The mixture passes though the matrix by pressure.

Optionally, after the mixture with the target molecule contacts the matrix, the target molecule bound matrix may be washed with a wash solution. The wash solution is typically PBS (phosphate buffered saline). The wash solution is able to remove unbound substances from the matrix.

The method of the present disclosure exhibits superior sensitivity than separations using conventional matrices. In one embodiment, the general sensitivity of an affinity extraction/separation using the chromatographic matrix of the present disclosure for a target molecule is less than about 500 pM, preferably less than about 250 pM, and more preferably less than about 100 pM. Similarly, the amount of protein detectable by an affinity extraction/separation using the chromatographic matrix of the present disclosure for a target molecule is less about 50 fmol, preferably less than about 25 fmol, and more preferably less than about 10 fmol.

The binding ligand may bind the target molecule using a number of different mechanisms including, but not limited to, covalent binding and non-covalent binding. Recovering the target molecule by contacting the matrix with an eluent may involve using conditions that break the ligant-target molecule complex, e.g. antibody-protein complex. Typically this is done by changing pH, either with acidic solution (below pH 5; preferably pH 3) or basic solution (above pH 8, preferably pH 9). The eluent may be aqueous or a nonaqueous solvent, such as methanol or acetonitrile, or water mixed with a nonaqueous solvent.

The present disclosure is useful for making a protein chromatography matrix which may be used in known methods of affinity chromatography, for example column separation and immunoprecipitation. In one embodiment, the sample solution is contacted with the affinity chromatography beads of the present disclosure and specific binding between the ligand and target molecule (e.g. ligand binding partner) occurs. Non-specifically bound material may be washed away from the beads by the mixture solution or by an optional wash step. Specifically bound material is recovered by elution or precipitation.

In a specific embodiment, the specifically bound material is subjected to a second round of affinity extraction to increase purification to improve selectivity by using complementary antibodies developed for ELISA. A second round may be done to avoid cross-reactivity of the ligand with other target molecules, e.g. the first antibody with other proteins. The second round may use a different ligand, e.g. antibody, chosen not to cross-react with the same unwanted proteins.

The chromatographic matrix described above provides a superior medium for affinity chromatography compared with currently available media such as agarose beads, which exhibit a high level of non-specific binding, and magnetic beads, which give low recovery of protein.

As shown in the following examples, coated silica particles (or beads), but not commercially available agarose or magnetic affinity beads, can be used to purify trace amounts of protein from biological fluids such as serum.

While preferred embodiments of the invention are described herein, it will be understood that such embodiments are provided by way of example only. Numerous variations will occur to those skilled in the art without departing from the spirit of the invention. Accordingly, it is intended that the appended claims cover all such variations as fall within the spirit and scope of the invention.

EXAMPLES

Example 1

Affinity Extraction of Ephrin Type-A Receptor 2 (EphA2) from Serum

Fluorescence-labeled EphA2, where EphA2 is a biomarker candidate for breast cancer, was spiked into 1.0 mL of sheep serum to a concentration of 10 ng/mL. Three affinity chromatography media were tested for the ability to extract EphA2 from the serum. The three extraction media were (1) silica particles coated with glycidoxylmethacrylate and acrylamide in a ratio of 1:20, respectively; prepared using 330 nm nonporous silica beads, to which a silane initator was bonded and the copolymer of acrylamide and glycidoxylmethacrylate was grown onto, and finally anti-EphA2 was attached; (2) commercially available magnetic beads (Invitrogen, now Life Technologies) to which the same anti-EphA2 was attached according to their written procedure; and (3) commercially available agarose beads (GE Healthcare) to which the same anti-EphA2 was attached according to their written procedure. Results are shown in Table 1.

In each case the commercial beads were used according to the instructions in their respective packages. The commercial beads and the silica beads were each mixed with 1 mL of EphA2 sample and allowed to equilibrate under gentle vortexing. The particles were gently centrifuged for the sepharose and silica beads, and a strong magnet was used to remove the beads in the case of the magnetic beads. The beads were re-suspended in phosphate buffered saline for rinsing, and then again centrifuged or removed by magnet. This washing step was performed at least three times. The EphA2 was recovered by releasing it from its antibody using triethylamine into a volume of 25 μL, and the EphA2 was analyzed by fluorescence. The beads were also tested in two sequential extractions, where a fresh set of beads were for a second extraction, after the pH of the released EphA2 solution was diluted into phosphate buffer solution to a volume of 1 mL. The results show that only the coated silica beads successfully recovered EphA2 from serum at a high enough level to allow a second extraction to improve protein purification.

TABLE 1

Recovery of EphA2 from serum

| Beads | Recovery after 1 extraction | Recovery after 2 extractions |
| --- | --- | --- |
| Silica | 94.0% ± 4% | 89.0% ± 5% |
| Agarose | 24.2% ± 5% | N.D |
| Magnetic | 35.1% ± 15% | N.D |

Figure 2:
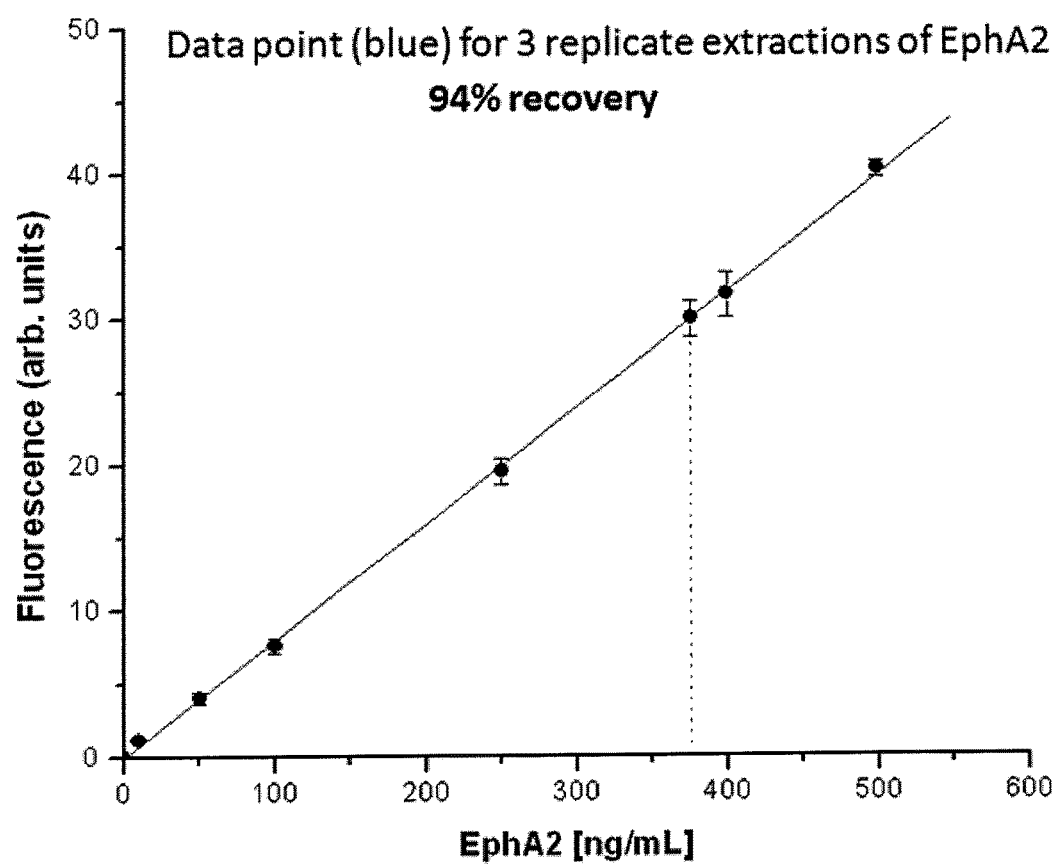
FIG. 2 shows a graph of the efficiencies of extraction of EphA2 present in sheep serum at 10 ng/mL by coated silica beads, magnetic beads, and agarose beads.

FIG. 2 shows that the coated silica affinity beads recovered 94% of the EphA2 from serum on the first extraction. The initial volume of the serum sample was 1.0 mL and eluted volume was 25 μL. The initial concentration was 10 ng/mL and the final concentration was 400 ng/mL. Data were obtained by comparison of EphA2 in the eluate to a calibration curve of standards.

Example 2

Affinity Extraction of Prostate Specific Antigen (PSA) from Serum

Figure 3:
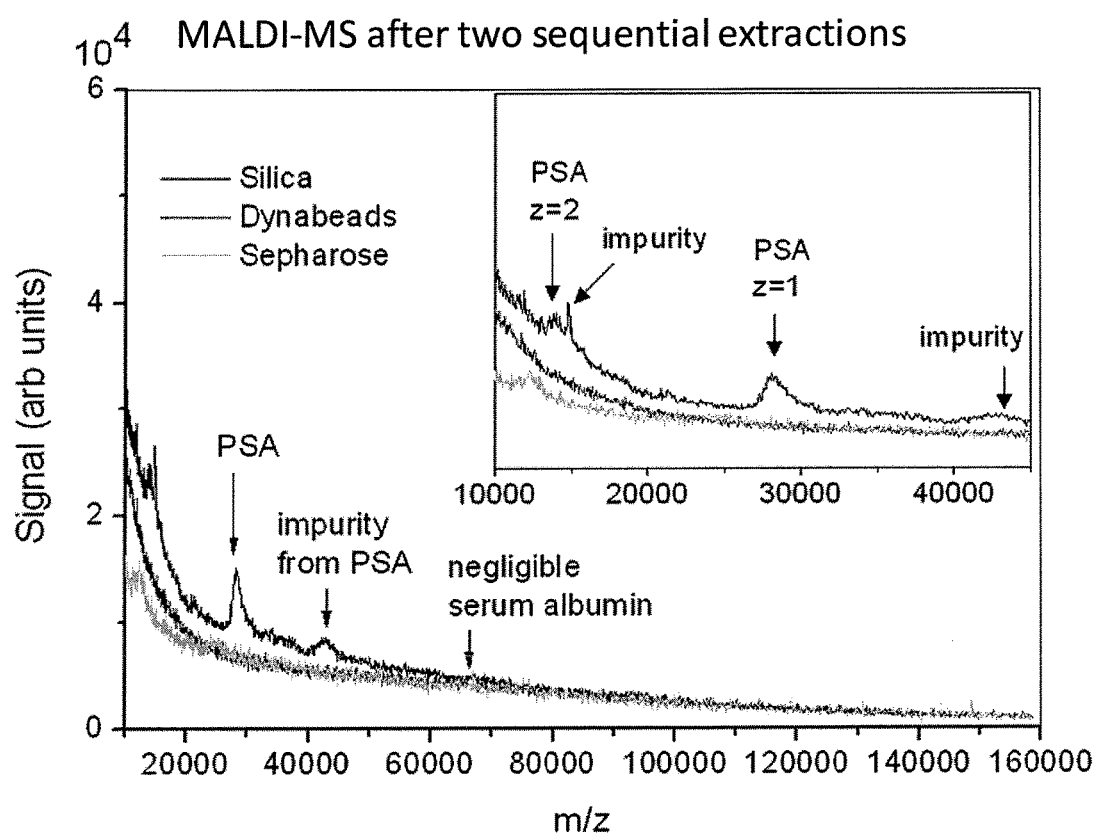
FIG. 3 shows a graph of the mass spectra of prostate specific antigen (PSA) after two extractions with coated silica beads, magnetic beads and agarose beads.

To substantiate the results of Example 1, human PSA was spiked into sheep serum to a concentration of 10 ng/mL and a 1.0 mL sample was extracted with coated silica beads, magnetic beads (Dynabeads), and agarose (Sepharose) beads. Extracted PSA was eluted into 25 μL of acetonitrile/water solution of trifluoroacetic acid and sinapinic acid. Mass spectra were determined from a 1 μL aliquot spotted onto a MALDI plate. Three replicate experiments were performed. As shown in the mass spectra of FIG. 3, only the coated silica beads successfully extracted measurable amounts of PSA. The mass spectrum shows that the disclosed method has high selectivity, meaning that there is negligible interference from serum proteins when the protein being analyzed is on the order of 10 ng/mL in concentration.

We claim:

1. An affinity chromatography matrix comprising
   a. a solid support, and
   b. a surface coating on the solid support, the surface coating comprising a copolymer, the copolymer comprising acrylamide and a second monomer comprising glycidoxylmethacrylate, methacrylate, or 2-(dimethylamino)ethyl methacrylate,
      wherein the molar ratio of glycidoxylmethacrylate to acrylamide in the copolymer is 20:1,
      wherein the molar ratio of methacrylate to acrylamide in the copolymer is 2:1, and
      wherein the molar ratio of 2-(dimethylamino)ethyl methacrylateto acrylamide in the copolymer is 2:1.

2. The matrix of claim 1, wherein the solid support comprises silicon dioxide.

3. The matrix of claim 1, wherein the solid support comprises a silicon dioxide particle or a silicon dioxide porous monolith.

4. The matrix of claim 1, wherein the solid support is a nonporous silicon dioxide particle.

5. The matrix of claim 1, wherein the solid support is a silicon dioxide particle having a diameter less than or equal to 2 μm.

6. The matrix of claim 1, the surface coating further comprising a binding ligand.

7. The matrix of claim 6, wherein the binding ligand is selected from the group consisting of streptavidin, protein A, protein G, an antibody, hexahistidine and a metal affinity agent.

8. A method for purifying or extracting a target molecule from a mixture comprising:
   a. contacting the mixture with a matrix comprising a solid support, a surface coating on the solid support, the surface coating comprising a copolymer and a binding ligand, the copolymer comprising acrylamide and a second monomer comprising glycidoxyimethacrylate, methacrylate, or 2-(dimethylarnino)ethyl methacrylate, wherein the binding ligand binds to the target molecule;
      wherein the molar ratio of glycidoxlmethacrylate to acrylamide in the copolymer is 20:1, wherein the molar ratio of methacrylate to acrylamide in the copolymer is 2:1, and
      wherein the molar ratio of 2-(dimethylamino)ethyl methacrylateto acrylamide in the copolymer is 2:1; and
   b. recovering the target molecule by contacting the matrix with an eluent which releases the target molecule from the ligand.

9. The method of claim 8, further comprising between steps a and b, contacting the matrix with a wash solution capable of removing unbound substances from the matrix.

10. The method of claim 8, wherein the mixture is blood serum, cell lysates, extracts of blood serum, extracts of cell lysates or protein pharmaceuticals.

11. The method of claim 8, wherein the target molecule comprises proteins, peptides, nucleic acids, glycoproteins and sugars.

12. The method of claim 8, wherein the method is able to purify or extract a target molecule from a mixture present in less than 500 pM.

13. The method of claim 8, wherein the method is able to purify or extract a target molecule form a mixture present in less than 50 fmol.

14. The matrix of claim 1, wherein the solid support is a silicon dioxide particle having a diameter between 50 nm and 500 nm.

15. The matrix of claim 1, wherein the solid support is a silicon dioxide particle having a diameter between 50 nm and 200 nm.

16. The matrix of claim 1, wherein the solid support is a silicon dioxide particle having a diameter between 300 nm and 500 nm.

* * * * *